(12) United States Patent
Brodaczewski et al.

(10) Patent No.: US 11,925,374 B2
(45) Date of Patent: Mar. 12, 2024

(54) LAPAROSCOPIC INSTRUMENT

(71) Applicant: KONMEX LIMITED LIABILITY COMPANY, Józefów (PL)

(72) Inventors: Wiesław Brodaczewski, Brentford (GB); Tomasz Przekopiński, Ząbki (PL); Grzegorz Wawryniuk, Warsaw (PL); Andrzej Decewicz, Nottingham (GB)

(73) Assignee: KONMEX LIMITED LIABILITY COMPANY, Józefów (PL)

( * ) Notice: Subject to any disclaimer, the term of this patent is extended or adjusted under 35 U.S.C. 154(b) by 631 days.

(21) Appl. No.: 17/132,800

(22) Filed: Dec. 23, 2020

(65) Prior Publication Data

US 2021/0322044 A1 Oct. 21, 2021

(30) Foreign Application Priority Data

Dec. 27, 2019 (PL) .......................... 432431

(51) Int. Cl.
| | |
|---|---|
| *A61B 17/29* | (2006.01) |
| *A61B 17/00* | (2006.01) |
| *A61B 17/3201* | (2006.01) |
| *A61B 18/00* | (2006.01) |
| *A61B 18/14* | (2006.01) |

(52) U.S. Cl.
CPC ...... *A61B 17/2909* (2013.01); *A61B 17/3201* (2013.01); *A61B 18/1445* (2013.01); *A61B 2017/00424* (2013.01); *A61B 2017/2903* (2013.01); *A61B 2017/2923* (2013.01); *A61B 2017/2925* (2013.01); *A61B 2017/2945* (2013.01); *A61B 2017/2946* (2013.01); *A61B 2018/00178* (2013.01)

(58) Field of Classification Search
CPC .............. A61B 18/1442; A61B 18/085; A61B 17/3201; A61B 10/02; A61B 2017/2946; A61B 2017/2923; A61B 2017/2837
See application file for complete search history.

(56) References Cited

U.S. PATENT DOCUMENTS 5,370,659 A * 12/1994 Sakashita ............... A61B 17/29
606/205

* cited by examiner

*Primary Examiner* — Shaun L David
*Assistant Examiner* — Rachael L Geiger
(74) *Attorney, Agent, or Firm* — Maschoff Brennan

(57) ABSTRACT

A laparoscopic instrument includes a handgrip and an articulated lever. A shank is attached to the handgrip at its closer end, and tissue acting actuators are installed at the further end of the shank. A string moves the actuators. A further end of the string is connected to the actuators, and a closer end is connected to the lever. The movement of the lever is coupled with movement of the actuators. The instrument has an integrated latching mechanism, which includes a toothed bar and a latch, holding the actuators in the operating position, and a locking and releasing mechanism equipped with a switching lever for holding and disengaging the latching mechanism. The switching lever is rotatably mounted on the handgrip and has a pushback element which, in the release position of the switching lever, disengages the latching mechanism move the toothed bar away from the latch.

20 Claims, 9 Drawing Sheets

LAPAROSCOPIC INSTRUMENT

The subject of the invention is the laparoscopic instrument.

In surgical operations on internal organs performed using the laparoscopic method, various types of surgical instruments are used to hold, deflect, incise the tissue of the operated organs or the organs connected to the operated organs. One of the most commonly used instruments is an instrument provided with tissue gripping pliers coupled with a mechanism to hold the jaws of the pliers in a fixed reciprocal operating position to ensure certain tissue compression, which must remain temporarily sustained due to the progress of the operation. The operating position is also understood to mean the holding of a tissue that allows temporary deflection of the tissue. Activities such as grasping and tissue incision can be performed many times during the operation, therefore the structure of the laparoscopic instrument should be ergonomic. There is an expectation that a laparoscopic instrument should be handled with one hand, for example with fingers of one hand.

Laparoscopic instruments provided with a handgrip are known from the state of the art, wherein the handgrip can be two-part, such as in scissors, for which pulling parts of the handgrip towards each other causes handling of the instrument's actuators. Instruments with a handgrip on which a lever for handling the actuators is attached are known. The instrument handgrips are equipped with mechanisms to hold the lever position.

The laparoscopic instrument is known from document EP0598607B1 which has a handgrip to which the handle is tightened to handling the pliers. The instrument is equipped with a latch mechanism comprising an arched toothed bar integrated in the handle and a latch arranged on the handgrip, wherein the latch covers a tooth on a longitudinal support. A deflection lever is installed on the handgrip, which is adapted to occupy two positions, wherein the lever holds continuous contact with the longitudinal support. In one position of the deflector lever, the toothed bar remains engaged with the tooth and in the other position deforms the longitudinal support so that the tooth is pushed back and out of the engagement so that the latching mechanism does not work. The disclosed latching mechanism is constructed from many elements, and in addition, the efficiency of this mechanism may be weakened with the loss of the elastic properties of the elements of which it is constructed.

Document EP2471472A1 discloses a laparoscopic instrument which comprises two pull handles which can be used to close and open the pliers. The handles are provided with a latching mechanism. Rotatably mounted latch in the form of a double lever is arranged on a fixed handle, which cooperates with an arched toothed bar fixed on a movable handle. One end of the lever is provided with a tooth, the other end of the lever is pushed up or down depending on whether the jaw position needs to be locked or released. The disclosed latching mechanism is also made of many elements and is too complicated in relation to its function.

Document EP2077774B1 discloses the tubular laparoscopic instrument for separating or cutting the tissue. Instrument is equipped with a latching mechanism, which comprises a toothed bar and a latch fixed on the handgrip and a lever tightened to it. The toothed bar acts as a flat spring and ensures that a latching mechanism remains in the locking position. The disclosed instrument does not have the lever to allow the latching mechanism to be disengaged permanently. In order to separate the latching mechanism elements, the operator of the instrument must tilt the toothed bar down with the other hand and hold it until the lever is completely tilted from the handle.

The object of the invention is a laparoscopic instrument comprising a handgrip and an articulated lever, shank which is attached to the handgrip at its closer end, tissue acting actuators installed at the further end of the shank, string to move the actuators, the further end of which is connected to the said actuators and the closer end is connected to the lever, with the string being placed inside the shank and the movement of the lever being coupled with movement of the actuators, in addition, the instrument is equipped with an integrated latching mechanism, comprising a toothed bar and a latch, designed to hold the actuators in the operating position by holding the lever position in relation to the handgrip, and a locking and releasing mechanism equipped with a switching lever to hold the latching mechanism to engage and to disengage the latching mechanism, characterized in that, the switching lever, which is rotatably mounted on the handle, is provided with a pushback element which, in the release position of the switching lever, disengage the latching mechanism in such a way that the toothed bar is moved away from the latch, wherein the pushback element rests against the toothed bar of the latching mechanism, while in the locking position the pushback element is moved away from the toothed bar of the latching mechanism.

Preferably, the instrument is provided with a knob turn indicator mechanism, which comprises a latching mechanism.

The latching mechanism is arranged in the handgrip, wherein the sphere element which determines the position of the knob makes a movement in the direction parallel to the axis of shank.

The switching lever can be fastened with latching pins in the first opening of the handle.

The shank of the instrument is preferably installed in a rotating position and the angular position of the shank in relation to the handgrip is set by means of a knob installed on the shank.

Preferably, actuators of the instrument are chosen from group comprising clamping jaws, window jaws, toothed jaws, hook jaws, scissors.

The instrument's lever is preferably provided with pins, which are adapted to be installed in the second openings in the handgrip.

The instrument's lever is preferably provided with the third opening, which is adapted to receive pivot element for string.

Preferably there is a fourth opening next to the third opening, to receive a cap of the third opening.

Preferably, the instrument is characterized in that the handgrip is provided with an electrical connector.

The handgrip and toothed bar are preferably made of a single plastic element.

The object of the invention is also the gripping and handling device for a laparoscopic instrument, which comprises handgrip and articulated lever, wherein the handgrip is adapted to attach the shank together with the actuators to act on tissue, wherein closer end of string adapted to move the actuators is articulated to the lever, wherein movement of actuators is coupled with movement of lever, in addition, the instrument is provided with an integrated latching mechanism, comprising a toothed bar and a latch, designed to hold the actuators in the operating position by holding the lever position in relation to the handgrip, and locking and releasing mechanism provided with switching lever to hold the latching mechanism to engage and to disengage the latching mechanism, characterized in that, the switching lever, which is rotatably mounted on the handgrip, is provided with a pushback element which, in release position of the switching lever, disengage the latching mechanism in such a way that toothed bar is moved away from the latch, wherein pushback element rests against toothed bar of the latching mechanism, while in locking position, the pushback element is moved away from the toothed bar of latching mechanism.

Preferably, the pushback element of the devices is made as bolt.

Preferably, the device is characterized in that, the handgrip is provided with a longitudinal opening adapted to receive the shank of the laparoscopic instrument.

The lever of the device is preferably provided with pins, which are adapted to be installed in the second openings in the handgrip.

The lever of the device is preferably provided with the third opening, which is adapted to receive the pivot element for the string.

Preferably, there is a fourth opening next to the third opening, to receive a cap of the third opening.

Preferably the handgrip of the device is provided with an electrical connector.

The handgrip and toothed bar are preferably made of a single plastic element.

Due to the integration of the latching mechanism elements and the locking and releasing mechanism with the handgrip and lever to a greater extent than in the case of known laparoscopic instruments, the number of mechanism elements has been reduced, which significantly reduces the cost of manufacturing the instrument according to the invention. The gripping and handling device is made up of a minimum number of elements, namely three elements, whereby elements of the instrument are designed to be made of plastic by injection molding using low-cost horizontal injection. The "latch" installation method simplifies the construction of the tool as much as possible, there is no need for additional mandrels, which also reduces installation costs. Due to very low manufacturing costs, the laparoscopic instrument, according to the invention, can be used as a disposable instrument, which significantly reduces the cost of treatment. The handgrip is made in such a way that it comprises a number of elements which were previously made as separate elements joined together during the assembly process. In addition, patient safety is increased by ensuring that tools are sterile. According to the invention, the laparoscopic instrument is ergonomic in use and is also safe for the patient, because triggering the latch, i.e. bringing the latch into engagement and disabling the latch, i.e. the latch is disengaged with use of the little finger, which does not involve the remaining fingers that can perform surgery activities without a break to change the position of the latch, which significantly increases the precision and certainty of movement during the work of surgeon. In other words, changing position of the latch and handling the instrument can be done in parallel. The latch position lever remains within reach of the small finger, regardless of the position of handgrip, in a place where it is impossible to accidentally trigger or disable the grip applied to the tissue, thus making the procedure performed by the surgeon smoother and safer. Moreover, the laparoscopic instrument, according to the invention, enables aural control of the change in angular position of the actuators of the pliers, both intentional caused by a surgeon and unintentional, which is appreciated, as the specificity of endoscopic procedures limits the surgeon to observe the movements of hands and instruments. In the instrument, according to the invention, the execution of the function of rotation through the shank of the instrument is clearly perceptible or heard by means of a series of clicks, which allows audible control of rotation of the actuators.

The object of the invention is described below in relation to the illustrated embodiment in the drawing, on which:

Figure 3:
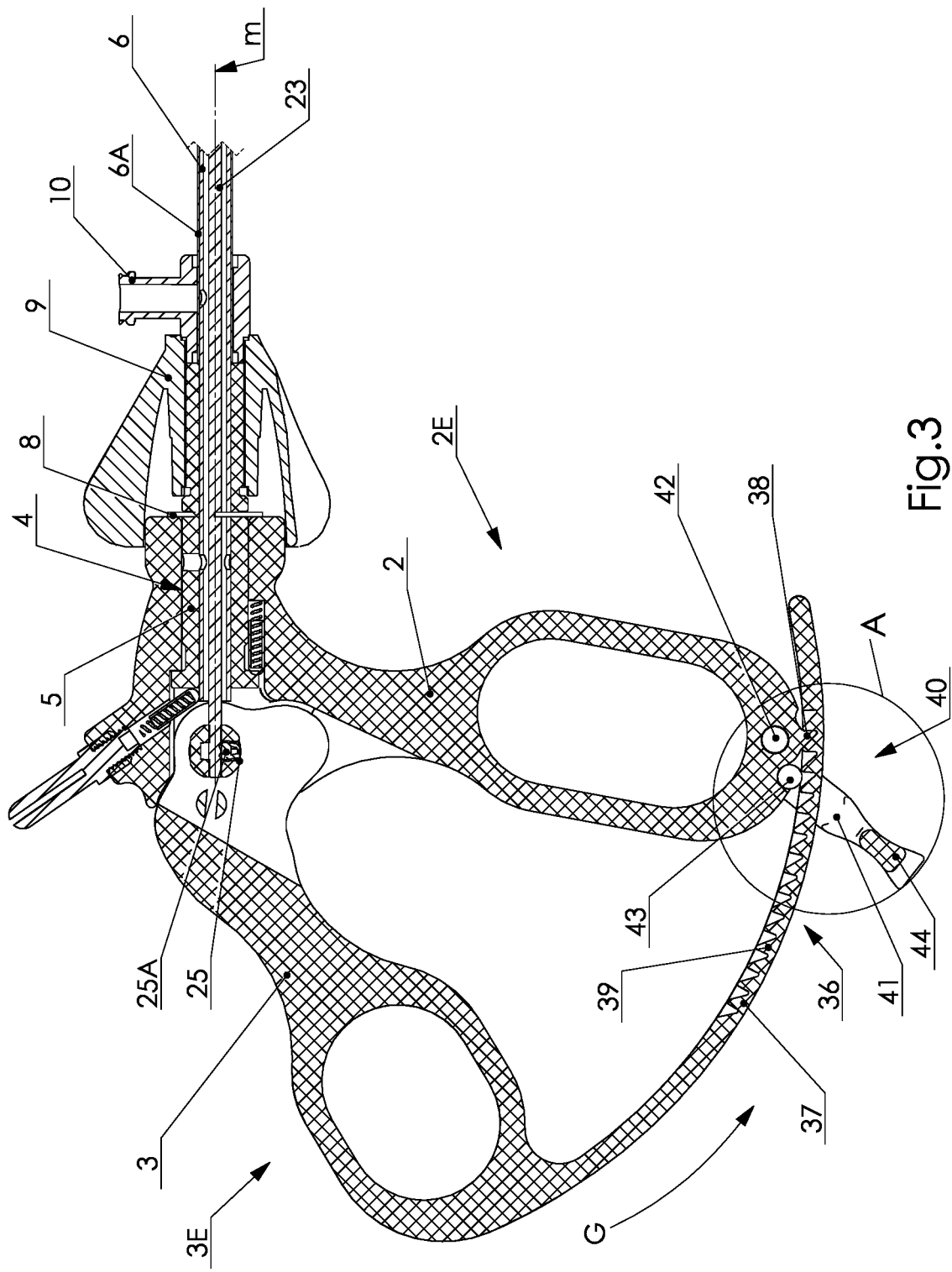
Figure 4:
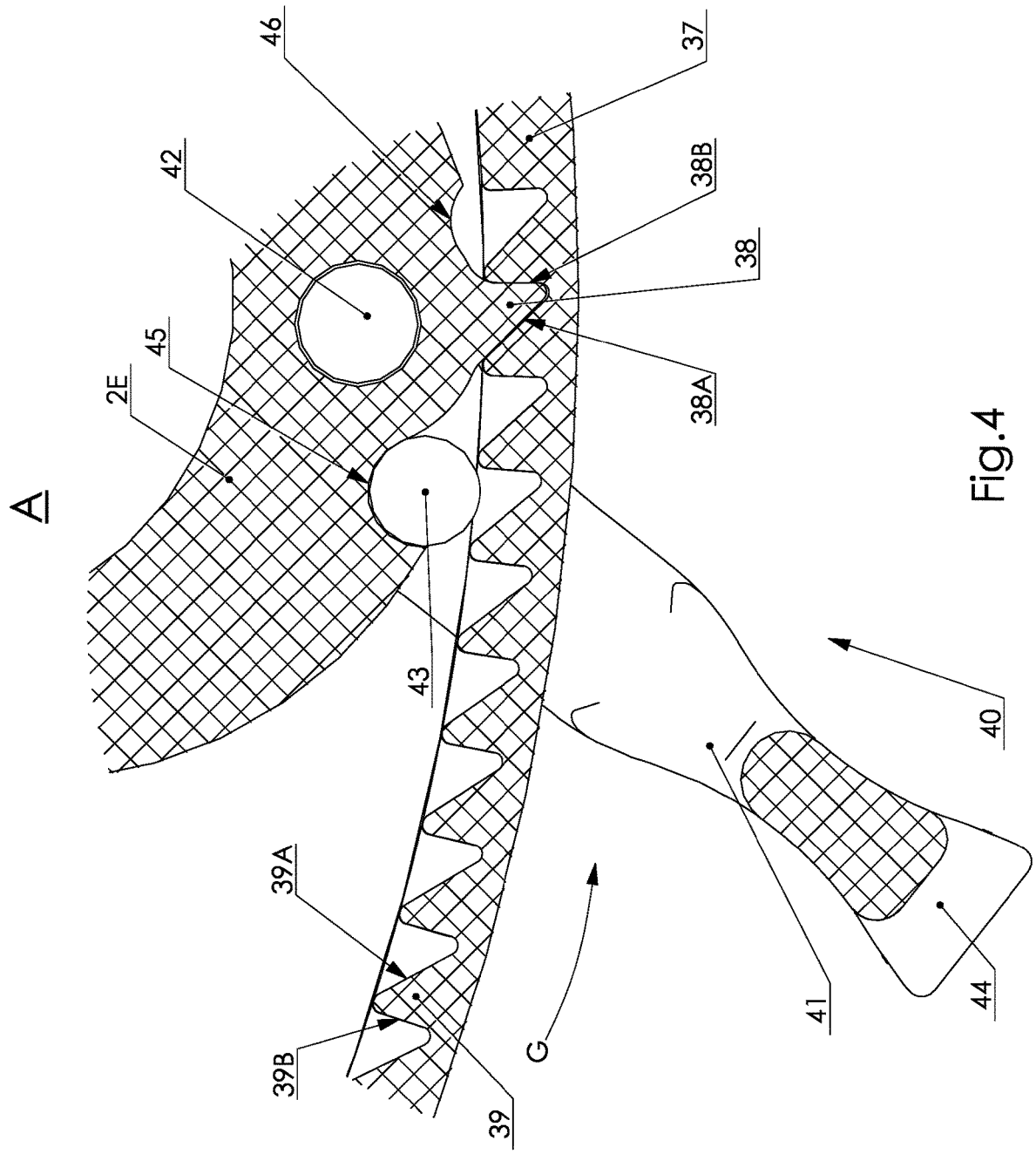
Figure 5:
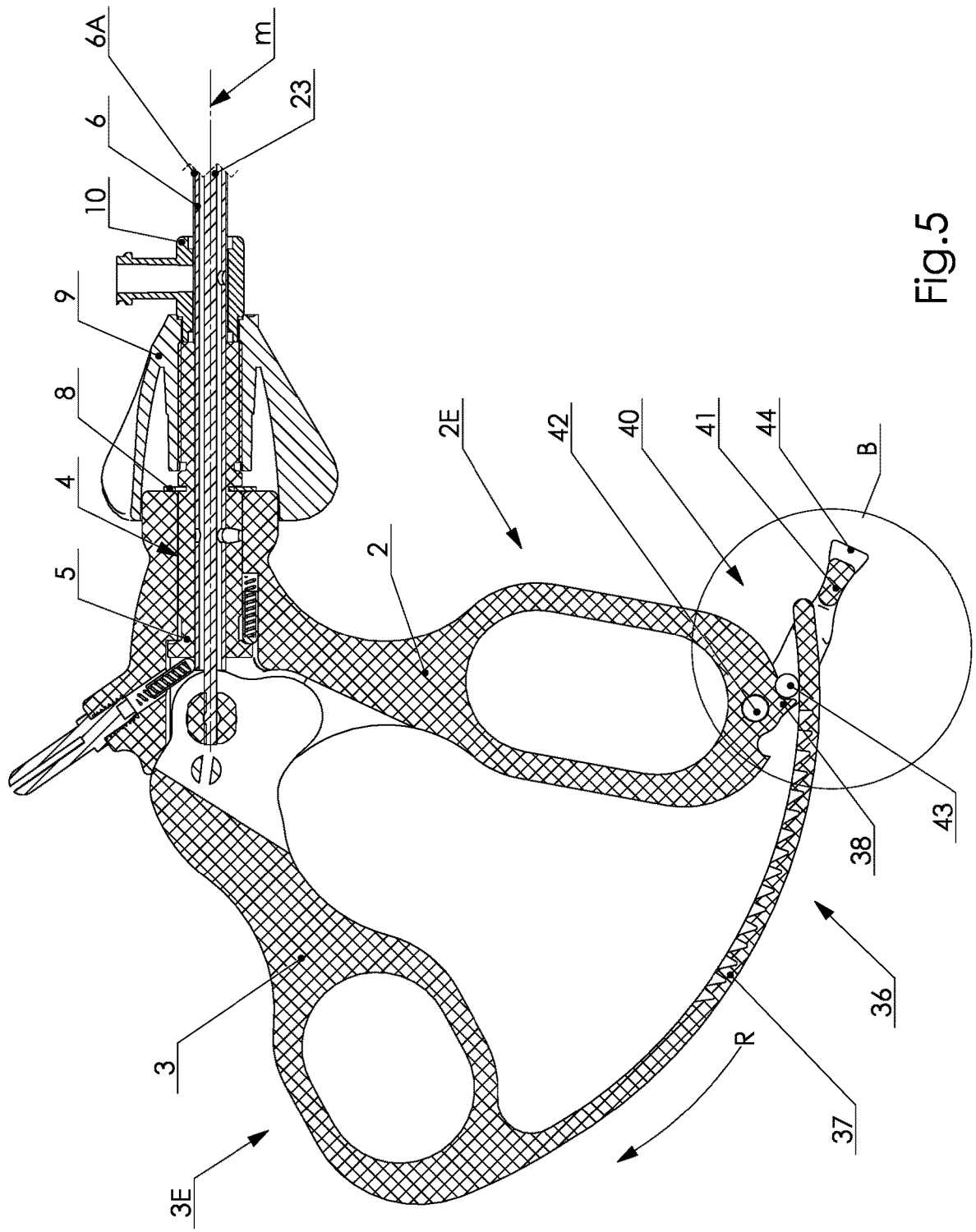
Figure 6:
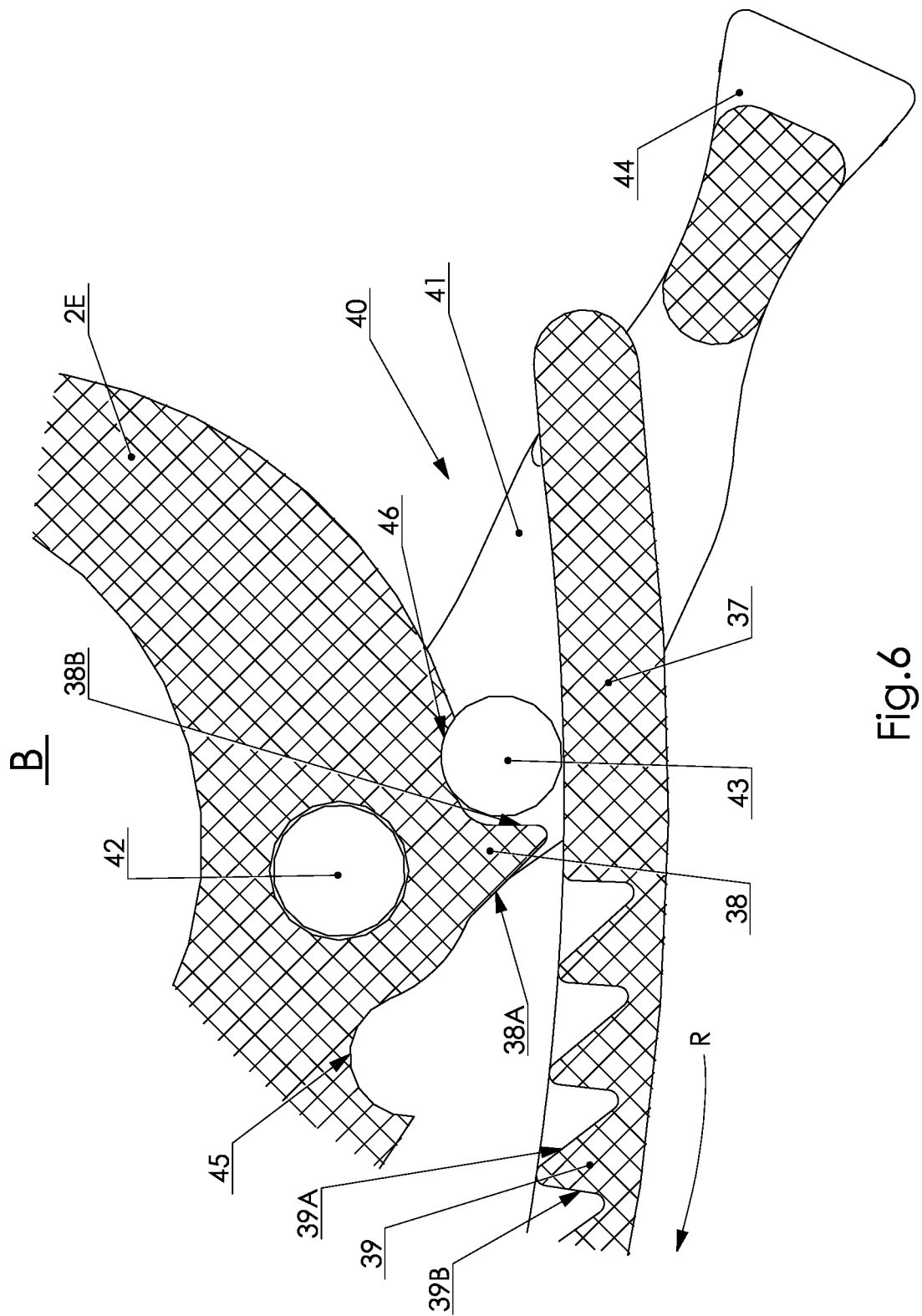
Figure 7:
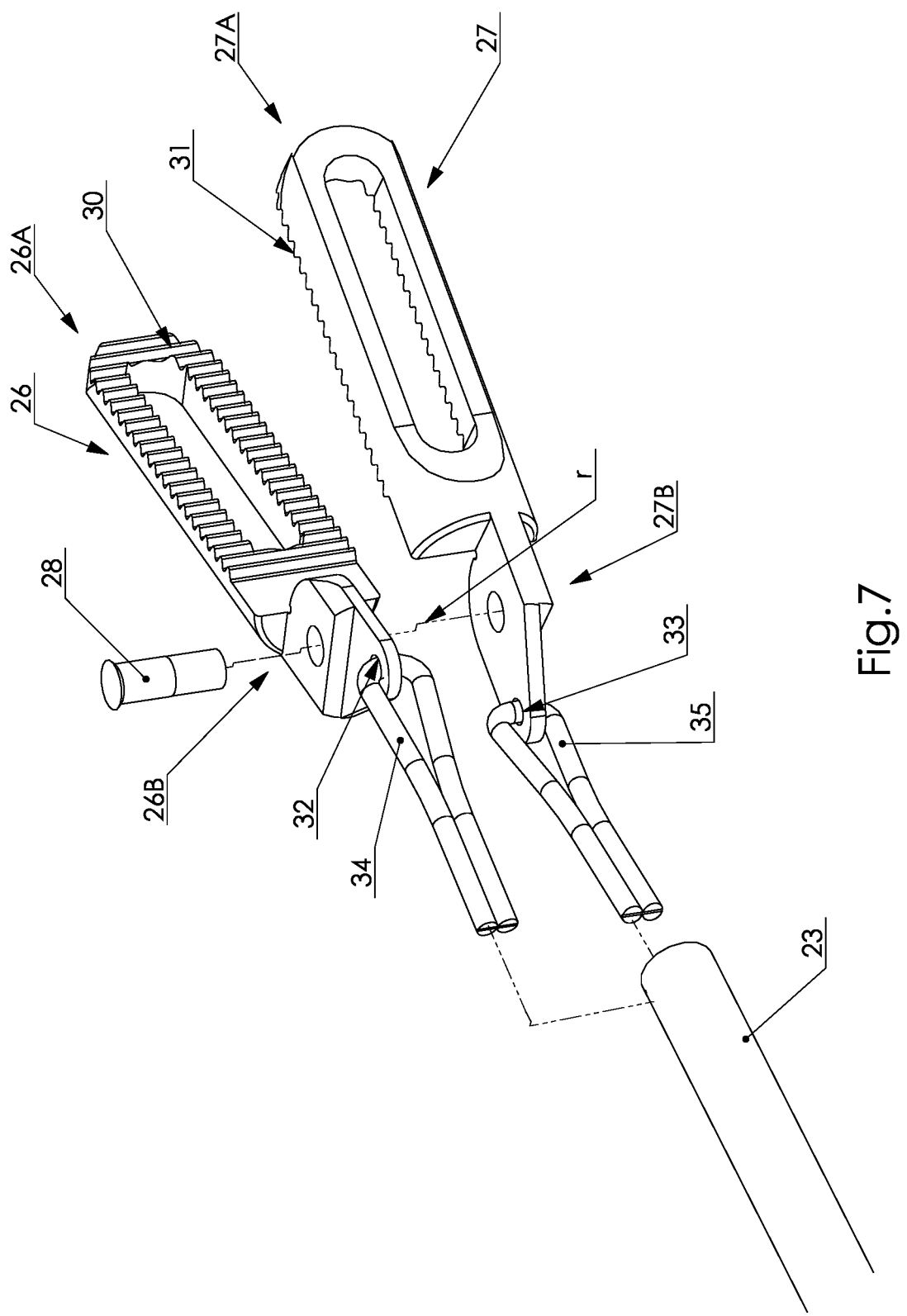
Figure 8:
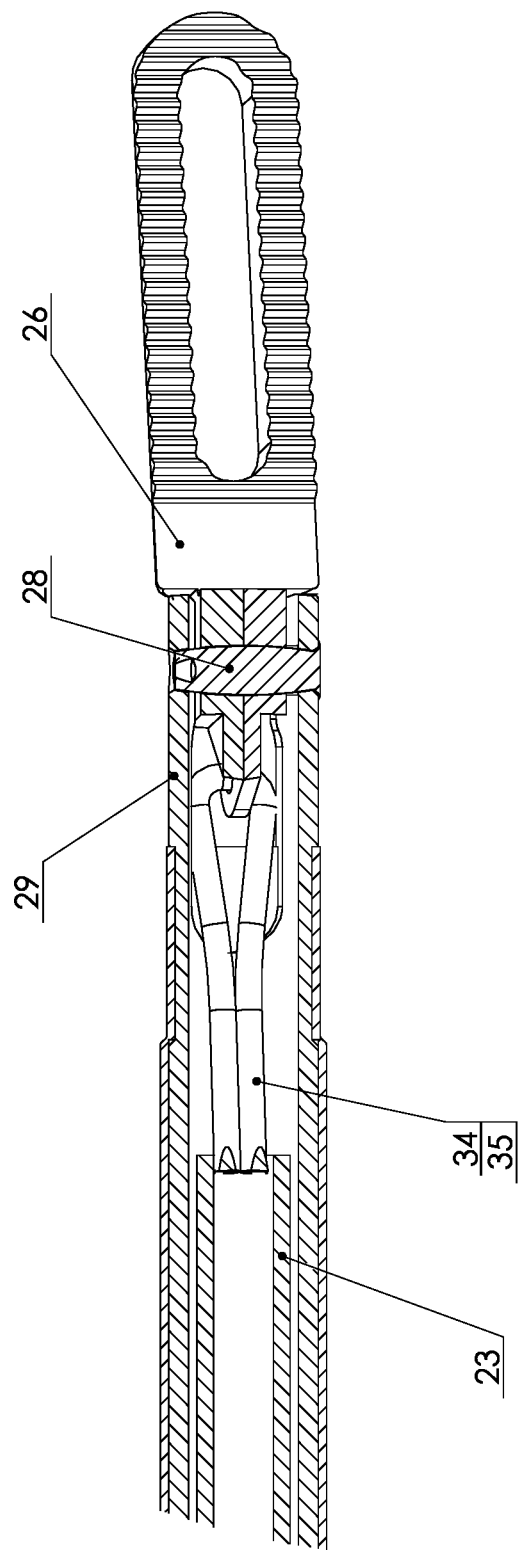
Figure 9:
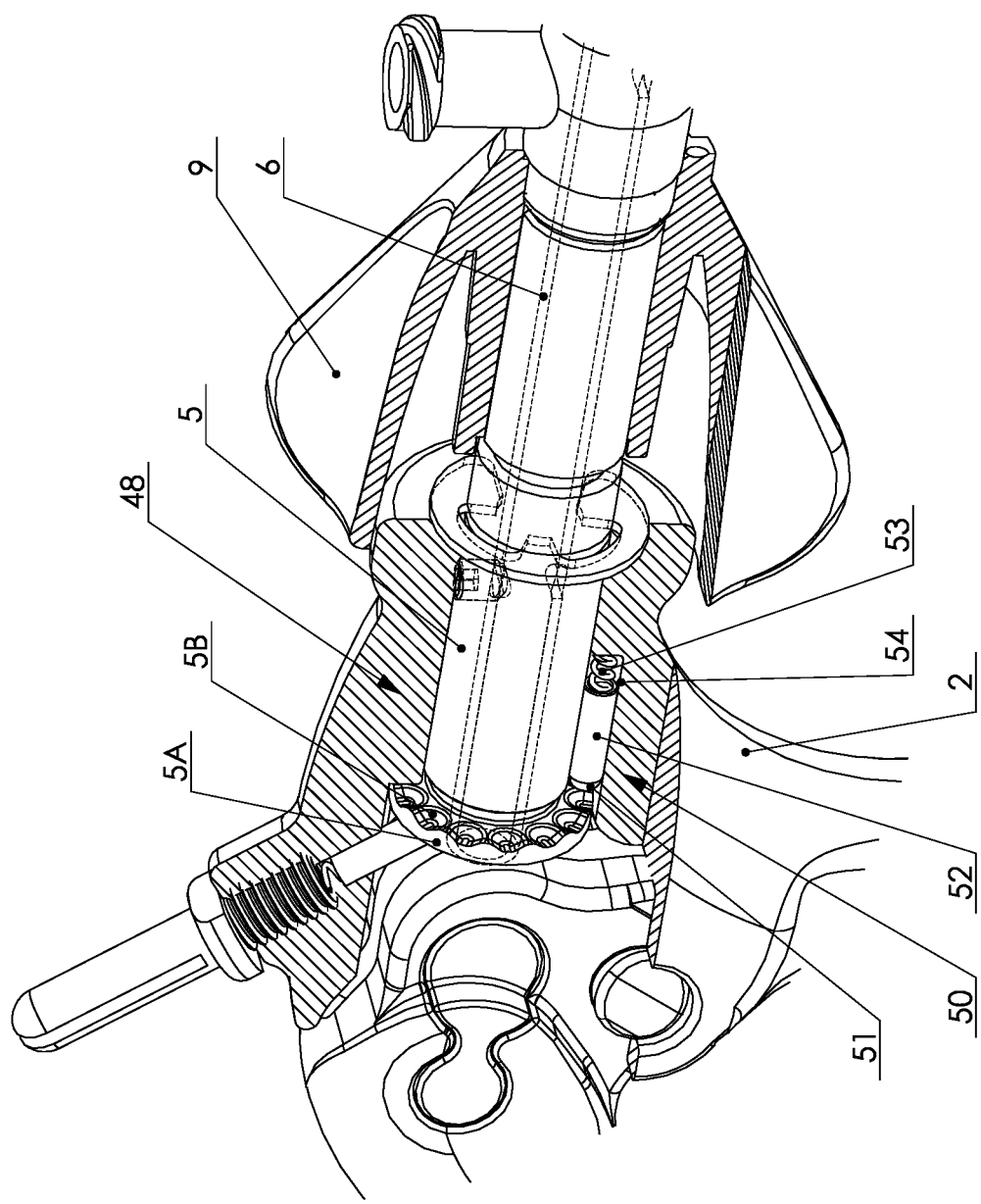

FIG. 3 shows the laparoscopic instrument in the longitudinal cross-section, wherein the locking and releasing mechanism is in the locking position, FIG. 4 shows an enlarged view from FIG. 3, FIG. 5 shows the laparoscopic instrument in the longitudinal cross-section, wherein the locking and releasing mechanism is in the releasing position, FIG. 6 shows an enlarged view from FIG. 5, FIG. 7 shows the clamping jaws in an enlarged view, FIG. 8 shows a cross-section through the shank of the instrument and the actuators, and FIG. 9 shows a cross-section through the knob rotation indicator mechanism.

In the description below the terms "closer" and "further" are used to refer to the longitudinal or arched like supporting or stringing elements of the instrument, wherein "closer" refers to the end of the longitudinal element on the side of the handgrip and "further" refers to the end of such element on the opposite side of the handgrip.

Figure 1:
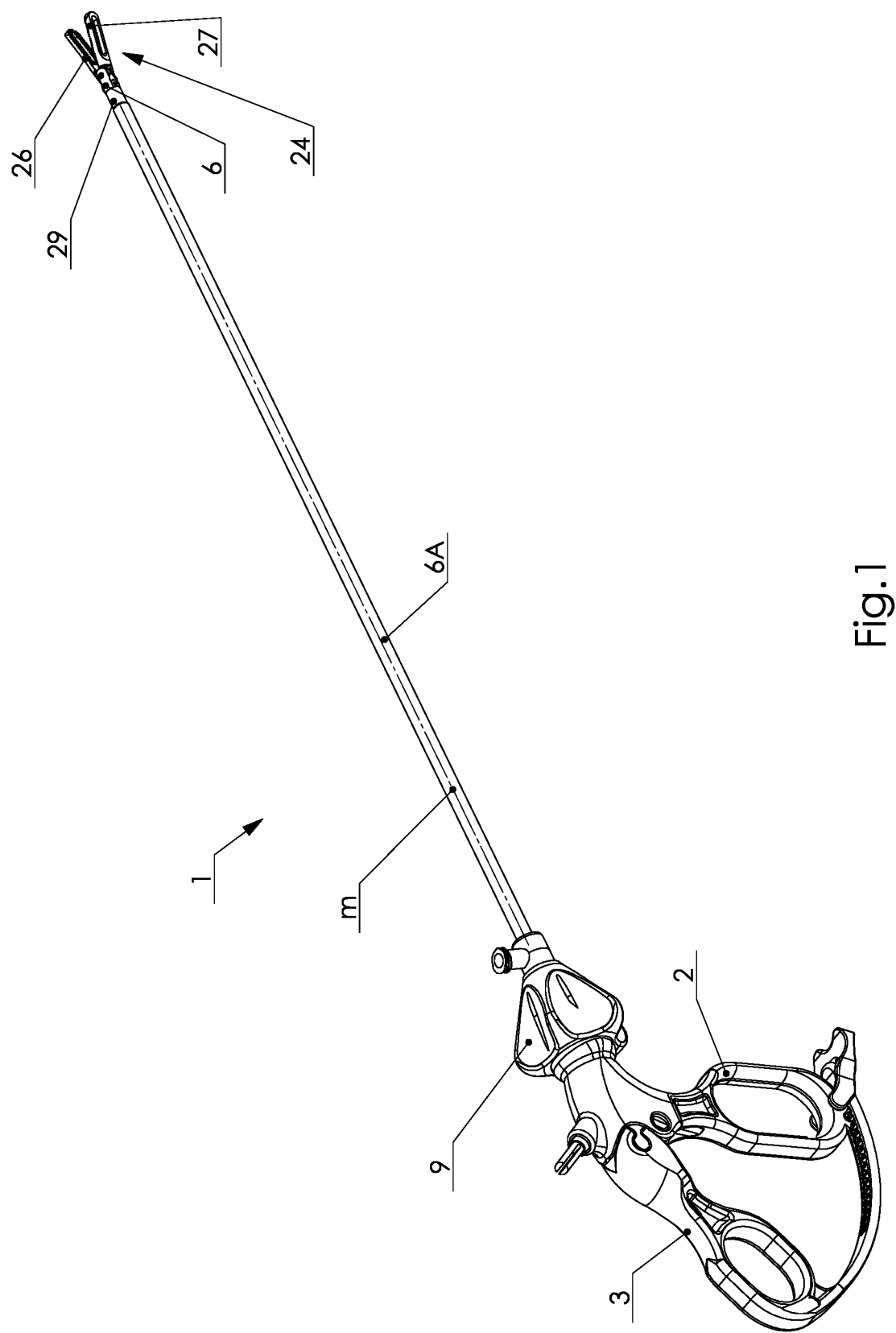
FIG. 1 shows the laparoscopic instrument in a perspective view.
Figure 2:
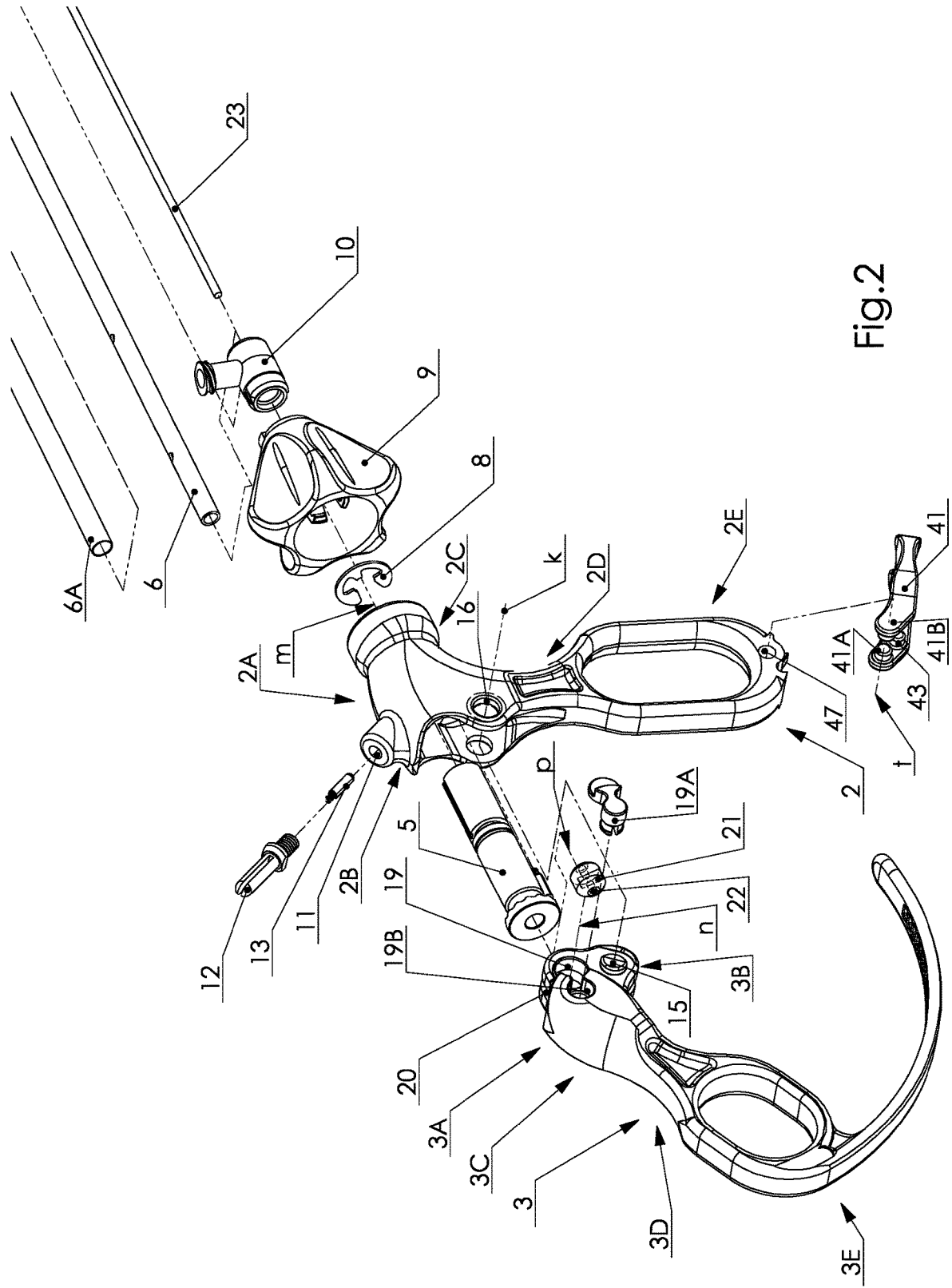
FIG. 2 shows the laparoscopic instrument in an exploded view.

The laparoscopic instrument 1 shown in FIG. 1 according to the first embodiment has handgrip 2 and lever 3 adapted to be operated by hand, wherein handgrip 2 and lever 3 are in the form of scissor-like handles, with finger openings. Lever 3 is operated with the thumb and the handgrip 2 is held with remaining fingers, wherein handgrip 2 is pointed downwards when using the laparoscopic instrument 1. Lever 3 and handgrip 2 are articulated to each other with their upper parts 3A and 2A (FIG. 2). In the upper part 2A of handgrip 2, there is a longitudinal cylindrical opening 4 (FIG. 3), in which the shank 6 with m axis is installed by means of sleeve 5, where position of sleeve 5 is determined in relation to the lever 3 by means of the settling ring 8, and the shank 6 in the form of a tube support passes through sleeve 5 centrally. Shank 6 is additionally supported by the knob 9, into which a spigot 10 is inserted and which is inserted on shank 6. The knob 9 is used to determine an angular position of shank 6 and the actuators of the laparoscopic instrument 1. In the upper part 2A of handgrip 2, there is an opening 11 arranged, in which a banana type electrical connector 12 is installed together with a spring latch 13. Electrical connector 12 presses spring latch 13 so that, by means of the spring tension, latch 13 holds frictional conductive connection to the shank 6, whereby, in the section from the knob 9 to the actuators of the laparoscopic instrument 1, shank 6 is surrounded by insulation foil 6A, for example, made of heat-shrinkable material. The laparoscopic instrument provided with an electrical connector can be used as monopolar instrument in laparoscopic surgery. Banana type electrical connector 12 is a standard connector used in electrosurgery to supply power to the actuators. Connector 12 is arranged at an angle of 55 degrees to the axis of shank 6, so that the power cord is positioned in a way that does not interfere with movement and precision of surgeon performing an operation. Lever 3 is installed to handgrip 2 and articulated on the k-axis. The lever 3 is provided in its upper part 3A with two coaxial pivots 15 arranged on two opposite sides of the articulation part 3B. The shaded articulation part 3B is arranged in the recess 2B of handgrip 2, wherein pivots 15 are being inserted in the second openings 16, whose k-axis passes through the walls of recess 2B, wherein in a position when the instrument is in use, the axis k is below the axis m of the shank 6. In the proximity of the shaded part 3B of lever 3 there is a wider section 3C of the upper part 3A of lever 3, in which, cylindrical third opening 19 with the n axis is made. In the upper part of 3A, a slotted notch 20 is made, plane of which is perpendicular to both the k-axis and the n-axis, with the k and n axes intersecting the slotted notch 20. In the third opening 19, a cylindrical pivot element 21 is arranged, in which through opening 22 with p axis is made, wherein the cylindrical pivot element 21 is inserted in the third opening 19 symmetrically in relation to the upper part 3A so that the axis p is arranged in the plane of symmetry of slotted notch 20 and in the axis k. The closer end of string 23 is inserted into through opening 22 to move pliers 24 of the laparoscopic instrument 1, pivot element 21 and the third opening 19 represent the joint for string 23. The close end of string 23 is clamped into cylindrical pivot element 21 in opening 25 by means of a pressure screw 25A. The third opening 19 is closed with a cap 19A latched in the fourth opening 19B arranged next to the third opening 19.

The laparoscopic instrument can be equipped with actuators selected from a group including: clamping jaws, window jaws, toothed jaws, hook jaws, scissors, in medical terminology known as graspers, dissectors and scissors of various types. The laparoscopic instrument shown in this example uses pliers 24, which comprises two window jaws 26, 27 which are rotatably mounted on the r-axis (FIG. 7) with shank 28, which is placed in the support 29 at the further end of shank 6 (FIG. 1). Each window jaw 26, 27 is made as a double lever, one arm respectively 26A, 27A has a clamping surface 30, 31, the other arm respectively 26B, 27B is equipped with an opening 32, 33, into which a susceptible string is inserted, respectively 34, 35. Strings 34, 35, for example braided steel cables, are connected to the further tube-shaped end of string 23 (FIG. 8) by clamping with a press the ends in the tube after having previously passed them through openings 32, 33.

Both, handgrip 2 and lever 3 form a gripping and handling device. Handgrip 2 is provided with the first center element 2D and the first gripping element 2E, while lever 3 is provided with the second center element 3D and the second gripping element 3E (FIG. 2). The laparoscopic instrument 1 is provided with a latching mechanism 36 comprising a toothed bar 37 and a tooth 38 cooperating with toothed bar and acting as a latch (FIG. 3). The arch-shaped toothed bar 37 is integrated with the second gripping element 3E, toothed bar 37 is provided with multiple teeth 39 adapted to cooperate with tooth 38 arranged on the first 2E gripping element. The toothed bar 37 is arranged in such a way that teeth 39 of the toothed bar 37 are in contact with tooth 38, i.e. engage the tooth 38. Both, teeth 39 and tooth 38 are triangular in shape. Between each of the teeth 39, there is a recess matching tooth 38. During the movement of pulling a lever 3 to a handgrip 2 marked as G, i.e. the second gripping element 3E to the first gripping element 2E, teeth 39 jump over the tooth 38, i.e. subsequent surfaces 39A of teeth 39 come into contact with the surface 38A of tooth 38 (FIG. 4), while the toothed bar 37 tilts to allow teeth 39 to jump over. The movement of lever 3 in G direction affects the gripping of the pliers, i.e. the gripping of lever 3 into handgrip 2 and brings the jaws 26, 27 or any other actuators closer together. Once the person performing the treatment has reached the required operating position, in this case clamping, i.e. the required position of the jaws 26, 27 relative to each other, and after stopping the tightening movement of lever 3 to handle 2, tooth 38 remains in the recess between teeth 39. Self-release movement of lever 3 and thus the of the clamp is not possible because the surface of 39B tooth 39 rests against the surface 38B of tooth 38. The Laparoscopic Instrument 1 is provided with a locking and releasing mechanism 40 which is designed to hold two positions—the locking position in which it is possible to clamp the pliers at any degree of clamping and to hold such clamping and the releasing position in which the person performing the operation can clamp the pliers and release the clamp freely, but it is not possible to hold the pliers being clamped. The locking and releasing mechanism 40 comprise a switching lever 41 articulated on the first gripping element 2E in the first opening 47 (FIG. 2), where the t-axis of joint 42 is essentially parallel to the k-axis and n-axis. Switching lever 41 is provided with a pushback element 43, which can hold a position depending on the position of switching lever 41 in the first socket 45 for the locking position or the second socket 46 for the release position (FIG. 4 and FIG. 6). Pushback element 43 is the movement limiter for switching lever 41, in the illustrated embodiment the pushback element 43 is a cylindrical bolt. Switching lever 41 is adapted to change its position from locking to releasing position and vice versa by pressing the tip 44. Joint 42 of switching lever 41 comprise two opposite pivots 41A arranged on the arms 41B of the switching lever 41. The arms 41B are flexible, allowing them to be tilted gently during the installation on a handgrip 2, so that the switching lever 41 is attached using a latch by inserting pins 41A into the first opening 47 in handgrip 2.

In the locking position of the locking and releasing mechanism 40 as shown in FIG. 3 and FIG. 4, the switching lever 41 is in the locking position and the latching mechanism 36 works as described above, i.e. it is possible to hold the appropriate operating position of the actuators, in the illustrated embodiment, clamping of the jaws 26, 27 of the pliers 24 of the of the laparoscopic instrument 1 by a person performing the operation. In FIG. 5 and FIG. 6 the locking and releasing mechanism 40 is in the releasing position, it is possible to withdraw lever 3 in the direction marked as R. Switching lever 41 is in the release position, where the pushback element 43 is resting against the second socket 46 of the gripping element 2E.

Handgrip 2, lever 3, cap 19A and switching lever 41 are made of one type of plastic, e.g. ABS, using the most cost-effective horizontal injection method. Handgrip 2 and toothed bar 37 can form a single piece obtained by this method.

The laparoscopic instrument is provided with a turn indicator mechanism 48 for knob 9 (FIG. 9), which comprises sleeve 5 inserted on shank 6 and a latching mechanism 50, wherein sleeve 5 is provided with a flange 5A with multiple recesses 5B, which are designed to cooperate with sphere element 51 of latching mechanism 50. Sphere Element 51 is inserted into the sleeve 52 and pressed against the flange 5A by a spring 53, wherein the sleeve 52 is placed in the handgrip 2 opening 54. Sphere element 51 has the ability to move in the direction parallel to the m-axis of handgrip 2. While setting the required position of the actuators by turning knob 9, the person performing the operation can hear a series of clicks of the latching mechanism 50. Regardless of aural evaluation of repositioning of the actuators, the person performing the operation senses with his or her hand a successive latching of the latching mechanism 50. The person performing the operation obtains an information about an intentional or accidental rotation of the actuators, which during the treatment are inside the patient, without the need to look at the handgrip of the laparoscopic instrument.

The invention claimed is:

1. A laparoscopic instrument comprising:
   a handgrip and an articulation lever,
   a shank which is attached to a closer end of the handgrip,
   actuators installed at a further end of the shank,
   a string to move the actuators, the further end of which is connected to the actuators and the closer end is connected to the articulation lever, wherein the string is placed inside the shank and the movement of the articulation lever is coupled with movement of the actuators, and
   an integrated latching mechanism, including:
      a toothed bar and a latch, designed to hold the actuators in an operating position by holding the articulation lever in position relative to the handgrip, and
      a locking and releasing mechanism equipped with a switching lever to hold the toothed bar of the latching mechanism to engage or to disengage the latching mechanism,
   wherein:
      the switching lever, which is rotatably mounted on the handgrip, is provided with a pushback element which,
      in a release position of the switching lever disengages the latching mechanism in such a way that the toothed bar is moved away from the latch, and in the release position
      the pushback element rests against the toothed bar of the latching mechanism,
      while in a locking position the pushback element is moved away from the toothed bar of the latching mechanism.

2. The instrument according to claim 1, wherein:
   the shank is rotatably installed; and
   an angular position of the shank in relation to the handgrip is set by means of a knob installed on the shank.

3. The instrument according to claim 2, further comprising a turn indicator mechanism for the knob.

4. The instrument according to claim 3, wherein the turn indicator mechanism comprises a latching mechanism.

5. The instrument according to claim 4, wherein:
   the latching mechanism is arranged in the handgrip; and
   a sphere element which determines a position of the knob makes a movement in a direction parallel to an axis of the shank.

6. The instrument according to claim 1, wherein the switching lever is attached with pivots into a first opening in the handgrip.

7. The instrument according to claim 1, wherein the actuators are chosen from the group consisting of clamping jaws, window jaws, toothed jaws, hook jaws, and scissors.

8. The instrument according to claim 1, wherein the articulation lever is provided with pivots, which are adapted to be installed in second openings in the handgrip.

9. The instrument according to claim 1, wherein the articulation lever is provided with a third opening, which is adapted to receive a pivot element for the string.

10. The instrument according to claim 1, wherein a fourth opening is positioned next to a third opening, to receive a cap of the third opening.

11. The instrument according to claim 1, wherein the handgrip is provided with an electrical connector.

12. The instrument according to claim 1, wherein the handgrip and the toothed bar are a single plastic element.

13. A gripping and handling device for a laparoscopic instrument, the gripping and handling device comprising:
    a handgrip and an articulation lever, wherein:
       the handgrip is adapted to attach a shank together with actuators to act on tissue,
       a closer end of a string adapted to move the actuators is clamped to the articulation lever by means of a cylindrical pivot element,
       movement of the actuators is coupled with movement of articulation lever,
       the instrument is provided with an integrated latching mechanism, including:
          a toothed bar and a latch, designed to hold the actuators in an operating position by holding the articulation lever position in relation to the handgrip, and
          a locking and releasing mechanism provided with a switching lever to hold the toothed bar of the latching mechanism to engage or to disengage the latching mechanism, wherein:
             the switching lever, which is rotatably mounted on the handgrip is provided with a pushback element which
             in a release position of the switching lever disengages the latching mechanism in such a way that the toothed bar is moved away from the tooth, and in the release position
             the pushback element rests against the toothed bar of the latching mechanism,
             while in a locking position, the pushback element is moved away from the toothed bar of the latching mechanism.

14. The device according to claim 13, wherein the pushback element made as a bolt.

15. The device according to claim 13, wherein the handgrip is provided with a first longitudinal opening adapted to receive the shank of the laparoscopic instrument.

16. The device according to claim 13, wherein the articulation lever is provided with pins, which are adapted to be installed in second openings in the handgrip.

17. The device according to claim 13, wherein the articulation lever is provided with a third opening, which is adapted to receive a pivot element for the string.

18. The device according to claim 13, wherein a fourth opening is positioned next to a third opening, to receive a cap of the third opening.

19. The device according to claim 13, wherein the handgrip is provided with an electrical connector.

20. The device according to claim 13, wherein the handgrip and the toothed bar are a single plastic element.

* * * * *